United States Patent [19]

Mahjour et al.

[11] Patent Number: 4,879,297

[45] Date of Patent: Nov. 7, 1989

[54] FATTY ACIDS AND THEIR SMALL CHAIN ESTERS AS PENETRATION ENHANCERS IN AQUEOUS SYSTEMS

[75] Inventors: Majid Mahjour, Netcong; Bernadette E. Mauser, Lyndhurst; Mahdi B. Fawzi, Flanders, all of N.J.

[73] Assignee: Warner-Lambert Company, Morris Plains, N.J.

[21] Appl. No.: 364,549

[22] Filed: May 23, 1989

Related U.S. Application Data

[63] Continuation of Ser. No. 056,520, Jun. 1, 1987, abandoned.

[51] Int. Cl.$^4$ ............................................. A61V 31/44
[52] U.S. Cl. ................................................... 514/282
[58] Field of Search ................................................ 514/282

[56] References Cited

FOREIGN PATENT DOCUMENTS 0171742 2/1986 European Pat. Off. .

OTHER PUBLICATIONS

Chem. Abst 104 (1986)-213272 T and 107(1987)-212096 P.

Primary Examiner—Stanley J. Friedman
Attorney, Agent, or Firm—Ronald A. Daignault

[57] ABSTRACT

Saturated or unsaturated fatty acids of 8-18 carbon atoms or a $C_1$-$C_4$ alkyl ester thereof in an aqueous system are described as skin absorption enhancers resulting in effective and non-irritating transdermal compositions comprising the above in combination with a therapeutically active ingredient.

10 Claims, No Drawings

FATTY ACIDS AND THEIR SMALL CHAIN ESTERS AS PENETRATION ENHANCERS IN AQUEOUS SYSTEMS

This is a continuation of Ser. No. 056,520, filed June 1, 1987, now abandoned.

BACKGROUND OF THE INVENTION

This invention relates to pharmaceutical compositions which are useful in effecting transdermal delivery of a therapeutic dose of a therapeutically active ingredient to the systemic circulation of a mammal.

As a specific and preferred application, therapeutically active ingredients or drugs such as opioids may be singled out as preferred active ingredients in such transdermal systems.

Many opioids are known to have poor bioavailability in the mammalian systemic circulation due to extensive initial metabolism of the drug by the liver and intestines. Furthermore, the bioavailability of orally administered opioids may be unpredictable since various factors such as changes in acidity and food content can cause changes in the amount of drug absorbed from the gastrointestinal tract. Also, oral administration does not necessarily insure good patient compliance.

Parenteral administration of opioids provides better bioavailability than oral administration. However, the various routes of parenteral administration such as intravenous, intramuscular, and subcutaneous delivery are not convenient for chronic therapy. This is particularly true for those opioids which exhibit short biological activity half-lives.

Topical formulations of opioids do not necessarily provide delivery of a therapeutic dose of the drug to the systemic circulation and thus provide poor or unpredictable bioavailability. Natural oils containing saturated or unsaturated fatty acids have been described in such topical formulations with drugs used for local anesthetic purposes.

Transdermal delivery of opioid drugs to the mammalian systemic circulation have been described as an alternative mode of administration which can provide the following advantages:

1. Improved and predictable bioavailability of the opioid as compared to oral administration since transdermal delivery avoids initial metabolism by the liver and intestines, and unpredictable absorption from the gastrointestinal tract.
2. A stable blood serum level of the drug resulting in a prolonged pharmacological effect similar to intravenous infusion.
3. Easily adjustable dosing rate which provides maximization of efficacy and minimization of side effects.
4. Easily removable drug source which provides rapid cessation of dosing and elimination of the drug from the body fluids.
5. Convenience of dosing which provides improved patient comfort as compared to parenteral administration and the possibility of greater patient compliance as compared to oral administration.

Transdermal drug delivery is distinguished from topical drug delivery by the fact that while a transdermal formulation is specifically designed to provide a predictable and therapeutically significant rate of delivery of the drug to the systemic circulation, a topical formulation is specifically designed to provide a therapeutic effect only to the local area to which the drug is applied. Furthermore, topical formulations are often designed to prevent any systemic delivery of the drug in order to minimize side-effects. However, even if the topical delivery of a drug does result in systemic absorption, the amount of drug delivery to the circulation is variable and uncontrolled.

European patent publication 0 171 742 describes such a system for the transdermal delivery of opioids using saturated or unsaturated fatty alcohols as acids or esters thereof with a carrier or vehicle such as propylene glycol resulting in an organic system, i.e. suspension or gel. The disadvantage of this system is that the use of propylene glycol or other known organic solvents causes irritation to the skin.

It has now been found that saturated or unsaturated fatty acids or esters thereof, such as linoleic acid, is effective as a skin absorption enhancer in purely aqueous systems thus leading to new and effective transdermal compositions without skin irritation.

SUMMARY OF THE INVENTION

Accordingly the present invention relates to a pharmaceutical composition adapted for transdermal delivery of a therapeutically effective amount of a drug to the systemic circulation of a mammal comprising an aqueous suspension containing:

a therapeutically effective amount of a drug or a pharmaceutically acceptable salt thereof;

an effective amount of a saturated or unsaturated fatty acid of 8-18 carbon atoms or a $C_1$-$C_4$ alkyl ester thereof, and a pharmaceutically acceptable excipient.

Another aspect of the present invention is a method for the transdermal delivery of a therapeutically effective amount of a drug to the systemic circulation of a mammal which comprises administering to said mammal in an aqueous suspension:

a therapeutically effective amount of a drug or a pharmaceutically acceptable salt thereof;

an effective amount of a saturated or unsaturated fatty acid of $C_8$-$C_{18}$ carbon atoms or a $C_1$-$C_4$ alkyl ester thereof, and a pharmaceutically acceptable excipient.

DESCRIPTION OF PREFERRED EMBODIMENTS

Although the present aqueous transdermal composition encompasses the combination with any drug, the preferred utility of such a composition is with opioids.

By the term "opioid" is meant any natural or synthetic opioid analgesic such as morphine, oxymorphone, fentanyl, merperidine, propoxyphene, or oxycodone; any natural or synthetic narcotic antagonist such as nalmefene, naloxone or naltrexone; any natural or synthetic mixed opioid agonist/antagonist such as nalbuphine, butorphanol, buprenorphine or pentazocine; or any pharmaceutically acceptable salt thereof.

By the term "pharmaceutically acceptable salt" is meant any non-toxic pharmaceutically suitable salt of an opioid which has therapeutic properties in mammals. Preparation of such salts is well-known to those skilled in pharmaceuticals. Pharmaceutically acceptable salts of opioids include acetates, naphthylates, tosylates, succinates, hydrochlorides, palmitates, stearates, oleates, pamoates, laurates, valerates, hydrobromides, sulfates, methane sulfonates, tartrates, citrates, and maleates.

The term "saturated or unsaturated fatty acid of 8-18 carbon atoms" means any such acid or ester thereof effective in enhancing the penetration of a drug through the mammalian skin. Preferred are linoleic and oleic acids and their $C_1$–$C_4$ alkyl esters. Most preferred is linoleic acid.

Pharmaceutically acceptable excipients are additional materials used in the compositions to bind the effective ingredients into a cream or lotion form suitable for administration on the skin per se or through known devices such as bandaids, tapes, patches, and the like. These excipients are, for example, carbopol 934, carbopol 940, carbopol 941, (B. F. Goodrich and Co. they are acrylic acid, water soluble resin polymers, with molecular weights of 3,000,000; 4,000,000; and 1,250,000 respectively); tween 20, (ICI Americas) polysorbate 20 polyoxyethylene 20 sorbitan monolaurate, or other tweens such as tween 40, tween 60, and tween 80, and other pharmaceutically acceptable emulsifiers such as polyethyleneglycol esters, e.g. polyethyleneglycol monolaurates, can also be used.

The effectiveness of the present invention is illustrated by the following examples and results illustrated in table form which compares the permeation of oxymorphone through hairless mouse skin from organic and aqueous enhancer systems containing linoleic acid.

EXAMPLES

| | Non Aqueous Systems | | | | |
|---|---|---|---|---|---|
| Formulation | Flux ($\mu g/cm^2/h$) | P (cm/sec $\times 10^6$) | Lag Time (h) | Maximum Solubility (mg/ml) | Maximum* Flux (PxSoly) |
| LA:PG:TA 20:30:50 | 66.6 | 3.49 | 3.5 | 130.17 | 1635.46 |
| LA:PG:TA 10:30:60 | 51.5 | 2.65 | 4.2 | 93.77 | 894.29 |
| LA:PG:TA 5:30:65 | 40.0 | 2.02 | 7.6 | 60.60 | 440.68 |
| PG:TA 37.5:62.5 | <3 | — | — | — | — |

| Aqueous Systems | | |
|---|---|---|
| Formulations (containing 5% w/w oxymorphone | Flux ($\mu g/cm^2/h$) | Lag Time (h) |
| LA 30% (0.3% Carbopol + 2.5% Tween 20) 70% | 667.45 | 6.8 |
| LA 20% (0.3% Carbopol + 2.5% Tween 20) 80% | 636.11 | 9.3 |
| LA 10% (0.3% Carbopol + 2.5% Tween 20) 90% | 672.76 | 4.3 |
| LA 5% (0.3% Carbopol + 2.5% Tween 20) 95% | 543.82 | 9.5 |
| LA 20% (2.5% Tween 20) 80% | 884.46 | 4.4 |
| 0.3% Carbopol | 38.31 | 17 |
| 0.3% Carbopol + 2.5% Tween 20 | 19.73 | 15.61 |

*Calculated based on Fick's Law (flux = permeability × concentration gradient; maximum flux = P × solubility of drug in donor solution), assuming Fick's Law holds.
Legend
LA = Linoleic Acid
PG = Propylene Glycol
TA = Triacetin Note: Since the aqueous systems are suspensions, they are constantly providing maximum availability of oxymorphone or permeation (i.e. maximum flux); therefore, to compare permeability data with the organic systems, maximum flux values had to be calculated. Using the premeability coefficients for 0.5% oxymorphone solutions in the linoleic acid:propylene glycol:triacetin mixtures, maximum fluxes were calculated by multiplying the saturation solubility of oxymorphone in the respective system by its corresponding permeability coefficient. However, it should be noted that the aqueous dispersions (5% w/w drug) became depleted of drug causing a plateau in cumulative average concentration versus time graphs, therefore, higher flux values may be anticipated with the aqueous systems.

As shown in the table, aqueous systems containing the model fatty acid, linoleic acid, effectively enhanced the permeation of a model drug through the skin. The usual dose of oxymorphone is 6–10 mg per day which would be adequately provided by any of the aqueous systems containing linoleic acid from a 10 $cm^2$ patch.

We claim:

1. A pharmaceutical composition adapted for transdermal delivery of a therapeutically effective amount of a natural or synthetic opioid to the systemic circulation of a mammal consisting essentially of an aqueous suspension containing:
   a therapeutically effective amount of a natural or synthetic opioid or a pharmaceutically acceptable salt thereof;
   an effective amount of a saturated or unsaturated fatty acid of 8–18 carbon atoms or a $C_1$–$C_4$ alkyl ester thereof, and a pharmaceutically acceptable excipient.

2. A composition according to claim, 1 wherein the opioid is morphine, oxymorphone, fentanyl, meperidine, propoxyphen, or oxycodone; a natural or synthetic narcotic antagonist such as nalmefene, naloxone, naltrexone, nalbuphine, butorphanol, buprenorphine or pentazocine; or a pharmaceutically acceptable salt thereof.

3. A composition according to claim 2, wherein the opioid is oxymorphone.

4. A composition according to claim 1, wherein the fatty acid is linoleic or oleic.

5. A composition according to claim 1, wherein the aqueous suspension contains up to 0.1–10% by weight of opioid.

6. A composition according to claim 1, wherein the aqueous suspension contains from about 1 to about 30% by weight of a saturated or unsaturated fatty acid of 8-18 carbon atoms or a $C_1$-$C_4$ alkyl ester thereof.

7. A composition according to claim 6, wherein the aqueous suspension contains from about 1 to about 20% by weight of linoleic or oleic acid or a $C_1$-$C_4$ alkyl ester thereof.

8. A composition according to claim 6, wherein the aqueous system contains about 1 to about 30% by weight of linoleic acid.

9. A composition according to claim 6, wherein the aqueous system contains about 10 to about 20% by weight of linoleic acid.

10. A method for the transdermal delivery of a therapeutically effective amount of a natural or synthetic opioid to the systemic circulation of a mammal which comprises administering to said mammal in an aqueous suspension;
   a therapeutically effective amount of a natural or synthetic opioid or a pharmaceutically acceptable salt thereof;
   an effective amount of a saturated or unsaturated fatty acid of $C_8$-$C_{18}$ carbon atoms or a $C_1$-$C_4$ alkyl ester thereof, and a pharmaceutically acceptable excipient.

* * * * *